(12) United States Patent
Limon

(10) Patent No.: US 7,135,038 B1
(45) Date of Patent: Nov. 14, 2006

(54) DRUG ELUTING STENT

(75) Inventor: Timothy A Limon, Cupertino, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/262,150

(22) Filed: Sep. 30, 2002

(51) Int. Cl.
A61F 2/06 (2006.01)

(52) U.S. Cl. .................... 623/1.15; 623/1.39; 623/1.42

(58) Field of Classification Search ............... 623/1.15, 623/1.43, 1.42, 1.46, 1.39
See application file for complete search history.

(56) References Cited

U.S. PATENT DOCUMENTS

| 4,459,252 | A |   | 7/1984  | MacGregor ............... 264/46.9 |
|-----------|---|---|---------|-----------------------------------|
| 5,059,211 | A |   | 10/1991 | Stack et al. ................. 606/198 |
| 5,104,404 | A | * | 4/1992  | Wolff ........................ 623/1.16 |
| 5,163,952 | A |   | 11/1992 | Froix ............................ 623/1 |
| 5,282,823 | A |   | 2/1994  | Schwartz et al. .......... 623/1.22 |
| 5,306,286 | A |   | 4/1994  | Stack et al. ................. 606/198 |
| 5,342,348 | A |   | 8/1994  | Kaplan ..................... 604/891.1 |
| 5,425,739 | A |   | 6/1995  | Jessen ....................... 606/155 |
| 5,464,650 | A |   | 11/1995 | Berg et al. .................... 427/2.3 |
| 5,514,154 | A |   | 5/1996  | Lau et al. ................... 606/195 |
| 5,527,337 | A |   | 6/1996  | Stack et al. ................. 606/198 |
| 5,569,295 | A |   | 10/1996 | Lam ........................... 606/198 |
| 5,603,721 | A |   | 2/1997  | Lau et al. ................... 606/195 |
| 5,605,696 | A |   | 2/1997  | Eury et al. .................. 424/423 |
| 5,629,077 | A |   | 5/1997  | Turnlund et al. ............. 442/38 |
| 5,700,286 | A |   | 12/1997 | Tartaglia et al. ............... 623/1 |
| 5,713,949 | A |   | 2/1998  | Jayaraman ..................... 623/1 |
| 5,722,984 | A |   | 3/1998  | Fischell et al. .............. 606/198 |
| 5,766,710 | A |   | 6/1998  | Turnlund et al. .......... 428/36.1 |
| 5,769,883 | A |   | 6/1998  | Buscemi et al. ................. 623/1 |
| 5,843,172 | A |   | 12/1998 | Yan ............................... 623/1 |
| 5,855,600 | A |   | 1/1999  | Alt ................................ 623/1 |
| 5,873,904 | A |   | 2/1999  | Ragheb et al. ................. 623/1 |
| 5,891,108 | A |   | 4/1999  | Leone et al. ................. 604/264 |
| 5,972,027 | A |   | 10/1999 | Johnson ........................ 623/1 |
| 5,980,972 | A |   | 11/1999 | Ding .......................... 427/2.24 |
| 6,042,606 | A | * | 3/2000  | Frantzen .................... 623/1.18 |
| 6,071,305 | A |   | 6/2000  | Brown et al. ................... 623/1 |
| 6,086,611 | A | * | 7/2000  | Duffy et al. ............... 623/1.35 |
| 6,120,536 | A |   | 9/2000  | Ding et al. ................. 623/1.43 |
| 6,120,847 | A |   | 9/2000  | Yang et al. .................. 427/335 |
| 6,129,755 | A |   | 10/2000 | Mathis et al. .............. 623/1.15 |
| 6,171,334 | B1 |  | 1/2001  | Cox ........................... 623/1.15 |
| 6,174,329 | B1 | *| 1/2001  | Callol et al. ............... 623/1.34 |
| 6,203,569 | B1 | *| 3/2001  | Wijay ........................ 623/1.15 |
| 6,206,915 | B1 |  | 3/2001  | Fagan et al. ............... 623/1.42 |
| 6,254,632 | B1 |  | 7/2001  | Wu et al. ................... 623/1.15 |
| 6,273,908 | B1 |  | 8/2001  | Ndondo-Lay .................. 623/1 |
| 6,273,910 | B1 |  | 8/2001  | Limon ....................... 623/1.15 |
| 6,273,913 | B1 |  | 8/2001  | Wright et al. .............. 623/1.42 |

(Continued)

FOREIGN PATENT DOCUMENTS

EP    0 627 226    12/1994

(Continued)

OTHER PUBLICATIONS

U.S. Appl. No. 09/695,022, filed Oct. 23, 2000, Wu et al.

Primary Examiner—Corrine McDermott
Assistant Examiner—Thomas Sweet
(74) Attorney, Agent, or Firm—Squire, Sanders & Dempsey L.L.P.

(57) ABSTRACT

Stents having struts with narrowed portions are described. The narrowed portions have a coating disposed thereon for the local delivery of a drug.

62 Claims, 3 Drawing Sheets

U.S. PATENT DOCUMENTS

| | | | |
|---|---|---|---|
| 6,287,628 B1 * | 9/2001 | Hossainy et al. | 427/2.3 |
| 6,299,604 B1 | 10/2001 | Ragheb et al. | 604/265 |
| 6,355,063 B1 | 3/2002 | Calcote | 623/1.42 |
| 6,379,381 B1 * | 4/2002 | Hossainy et al. | 623/1.42 |
| 6,395,326 B1 * | 5/2002 | Castro et al. | 427/2.24 |
| 6,416,543 B1 * | 7/2002 | Hilaire et al. | 623/1.16 |
| 6,506,437 B1 * | 1/2003 | Harish et al. | 427/2.25 |
| 6,540,774 B1 * | 4/2003 | Cox | 623/1.15 |
| 6,551,353 B1 | 4/2003 | Baker et al. | 623/1.42 |
| 6,605,110 B1 * | 8/2003 | Harrison | 623/1.15 |
| 6,887,266 B1 * | 5/2005 | Williams et al. | 623/1.16 |
| 2002/0004679 A1 | 1/2002 | Eury et al. | 623/1.15 |
| 2002/0038145 A1 | 3/2002 | Jang | 623/1.15 |
| 2002/0068969 A1 * | 6/2002 | Shanley et al. | 623/1.16 |
| 2002/0082680 A1 * | 6/2002 | Shanley et al. | 623/1.16 |

FOREIGN PATENT DOCUMENTS

| | | |
|---|---|---|
| EP | 0679372 A2 * | 2/1995 |
| EP | 0 850 651 | 7/1998 |
| EP | 0 875 218 | 11/1998 |
| JP | 11299901 | 11/1999 |
| WO | WO 90/01969 | 3/1990 |
| WO | WO 98/23228 | 6/1998 |
| WO | WO 99/16386 | 4/1999 |
| WO | WO 01/00112 | 1/2001 |
| WO | WO 01/91918 | 12/2001 |

* cited by examiner

DRUG ELUTING STENT

BACKGROUND

This invention relates to implantable medical devices, such as stents. More particularly, this invention relates to a stent having drug delivery capabilities.

Percutaneous transluminal coronary angioplasty (PTCA) is a procedure for treating heart disease. A catheter assembly having a balloon portion is introduced into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the procedure includes formation of intimal flaps or torn arterial linings that can collapse and occlude the conduit after the balloon is deflated. Moreover, thrombosis and restenosis of the artery can develop over several months after the procedure, which can require another angioplasty procedure or a surgical bypass operation. To reduce the partial or total occlusion of the artery by the collapse of arterial lining and to reduce the chance of the development of thrombosis and restenosis, an intraluminal prosthesis, an example of which includes an expandable stent, is implanted in the lumen to maintain the vascular patency. Stents are scaffolding structures, usually cylindrical or tubular in shape, functioning to physically hold open, and if desired, to expand the wall of the passageway. Typically stents are capable of being compressed for insertion through small cavities via small catheters, and then expanded to a larger diameter once at the desired location.

To treat the damaged vasculature tissue and further fight against thrombosis and restenosis, there is a need to administer therapeutic substances to the treatment site. For example, anticoagulants, antiplatelets and cytostatic agents are commonly used to prevent thrombosis of the coronary lumen, to inhibit development of restenosis, and to reduce post-angioplasty proliferation of the vascular tissue. To provide an efficacious concentration to the treated site, systemic administration of medication can produce adverse or toxic side effects for the patient. Local delivery is a highly suitable method of treatment in that smaller levels of medication, as compared to systemic dosages, are concentrated at a specific site. Local delivery produces fewer side effects and achieves more effective results.

One commonly applied technique for the local delivery of the drugs is through the use of medicated stents. One method of medicating stents involves the use of a polymeric carrier coated onto the body of the stent. A polymer dissolved in a solvent and a drug added thereto can be applied to the stent. Once the solvent evaporates, a coating of the polymer containing the drug remains on the stent. The embodiments of the present invention provide various stent structures for containing a coating, such as a polymeric coating, for the local delivery of a drug.

SUMMARY

In accordance with one embodiment, a stent is disclosed comprising a strut having a first segment, a second segment and a third segment located between the first and second segments, wherein the transverse cross sectional area of the third segment is less than the transverse cross sectional area of the first segment and the second segment; and a coating disposed on the third segment of the strut, wherein the first and second segments of the strut are free of any coating. In one embodiment, the coating is disposed all the way around the third segment of the strut. The outer surface of the coating should not extend beyond the outer surface of the first or second segment of the strut. The coating can be made from a polymeric material containing a therapeutic substance. In accordance with one embodiment, the strut includes a linear segment extending into a curved segment, wherein the first, second and third segments define a part of the linear segment of the strut. The curved segment can include a notch or can be smaller in thickness or width than the first or second segment of the strut.

In accordance with another embodiment of the invention, a radially expandable stent is provided comprising a strut, at least a segment of the strut having a circumference smaller than the circumference of a remaining portion of the strut; and a coating supported by the segment of the strut having the smaller circumference. The strut can include four sides, wherein the width of the segment of the strut having the smaller circumference is less than the width of the remaining portion of the strut. Alternatively, the thickness of the segment of the strut having the smaller circumference is less than the thickness of the remaining portion of the strut. The coating can, for example, surround the segment of the strut having the reduced circumference. The remaining portion of the strut having the larger circumference can be free from any coating.

In accordance with another embodiment of the invention, a method of manufacturing a drug eluting stent is provided, comprising depositing a coating on a first segment of a strut of the stent, the stent including a second segment and a third segment, wherein the first segment is positioned between the second segment and the third segment, the first segment having a smaller transverse cross sectional area than the transverse cross sectional area of the second or third segment.

In accordance with another embodiment of the invention, a method of manufacturing a drug eluting stent is provided, comprising depositing a coating on a stent, the stent including a strut having a first segment, a second segment, and a third segment located between the first and second segments, wherein the transverse cross sectional area of the third segment is less than the transverse cross sectional area of the first segment and the second segment; and removing the coating off of the first and second segments so that the coating remains on the third segment.

DETAILED DESCRIPTION

Figure 1:
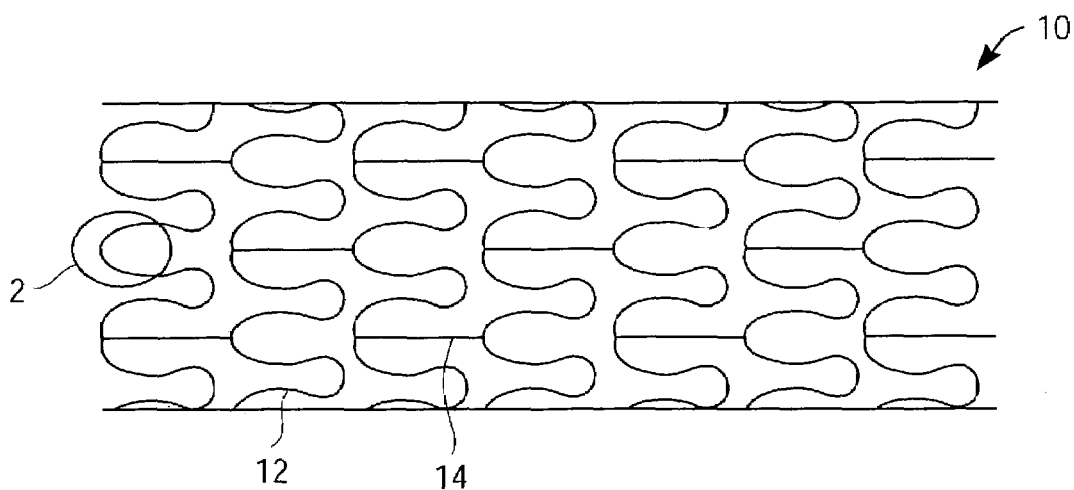
FIG. 1 illustrates an embodiment of a conventional stent.

FIG. 1 illustrates one embodiment of a stent 10 that can be used with the practice of the present invention. Stent 10 can be generally cylindrical and radially self- or balloon-expandable. Stent 10 can be inserted and deployed in a patient with an appropriate delivery device such as a balloon dilatation catheter. Stent 10 can be made, for example, from a plurality of wave-like or serpentine-like struts 12 having curved segments and generally linear segments. Struts 12 are connected to the adjacent struts 12 via connecting elements 14. The embodiments of the present invention, however, should not be limited to the structure of FIG. 1. A variety of other scaffolding designs can also be used, such as "V" shaped struts or struts having a "zigzag" formation.

Figure 2:
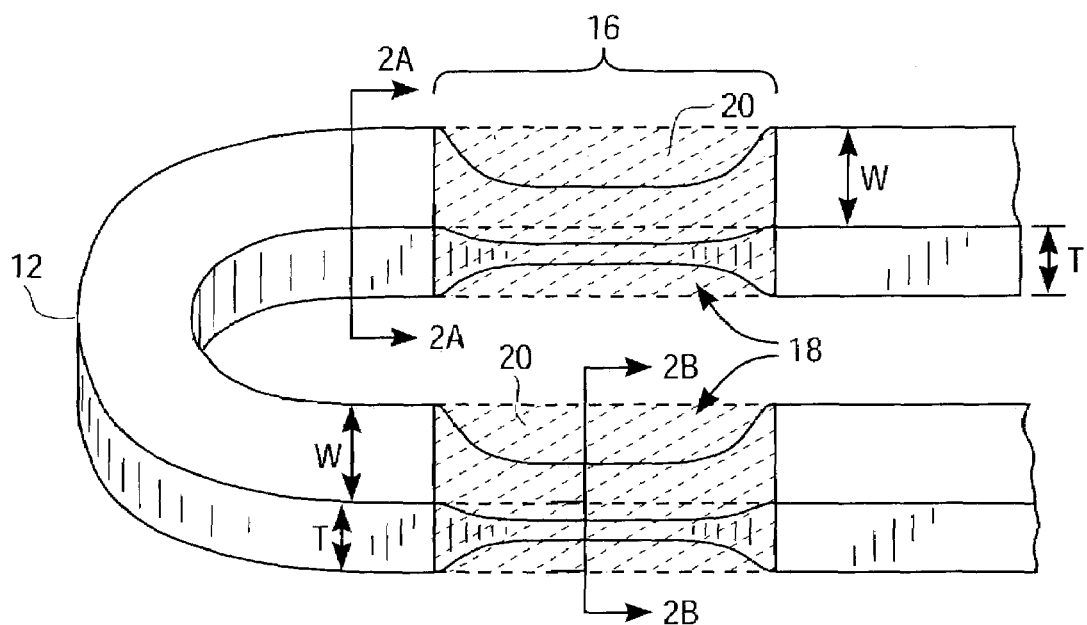
FIG. 2 is an enlarged perspective view of the stent strut of encircled region 2 of FIG. 1.
Figure 2A:
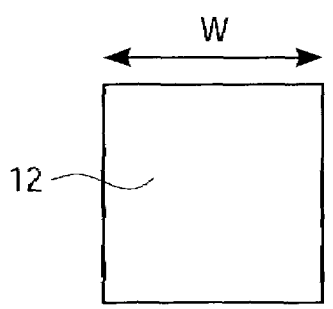
FIGS. 2A and 2B are transverse cross sectional views along the line 2A—2A and 2B—2B, respectively, of FIG. 2.
Figure 2B:
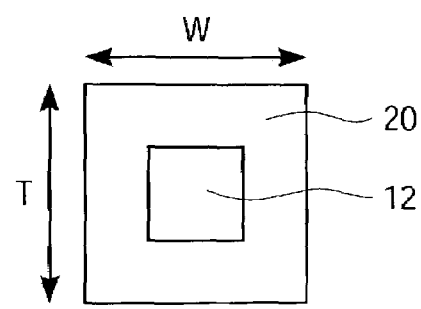

Referring to FIG. 2, the linear section of strut 12 includes a segment, referred to by reference number 16, wherein any transverse cross sectional portion of segment 16 has a smaller cross sectional surface area than the remaining segment of strut 12. FIG. 2A illustrates a transverse cross sectional view of strut 12 of FIG. 2 taken along the line 2A—2A. FIG. 2B illustrates a transverse cross sectional view of strut 12 of FIG. 2 taken along the line 2B—2B. As illustrated by FIGS. 2A and 2B, segment 16 has a reduced thickness and width, which provides for a smaller circumference, as compared to the remaining portions of strut 12.

FIGS. 2, 2A and 2B illustrate a four-sided strut 12 wherein segment 16 has a reduced width W as well as thickness T. Struts 12 need not be four-sided, however, and can have any suitable transverse cross sectional geometry, such as a three sided, oval or circular struts. The reduced circumferential size of segment 16 defines a recessed volume 18 in which a coating 20 can be deposited. Coating 20 can be a drug or a therapeutic composition or can contain the drug. Coating 20 can be made from any suitable biocompatible polymer, examples of which are disclosed below. As best illustrated by FIG. 2, the remaining segments of strut 12 can be free from any substances or coatings. Coating 20 can be disposed all the way around segment 16 as coating 20 can completely encapsulate the narrowed segment 16 of strut 12. Recessed volume 18 can be fully filled with the coating substance such that the outer surfaces of coating 20 are "flush" with their respective outer surfaces of strut 12. In other words, the outer dimensions of coating 20 can equal the outer dimensions of strut 12, thereby creating a smooth transition between the surfaces of coating 20 and the surfaces of strut 12, thus minimizing intravascular flow turbulence around stent 10.

Figure 3:
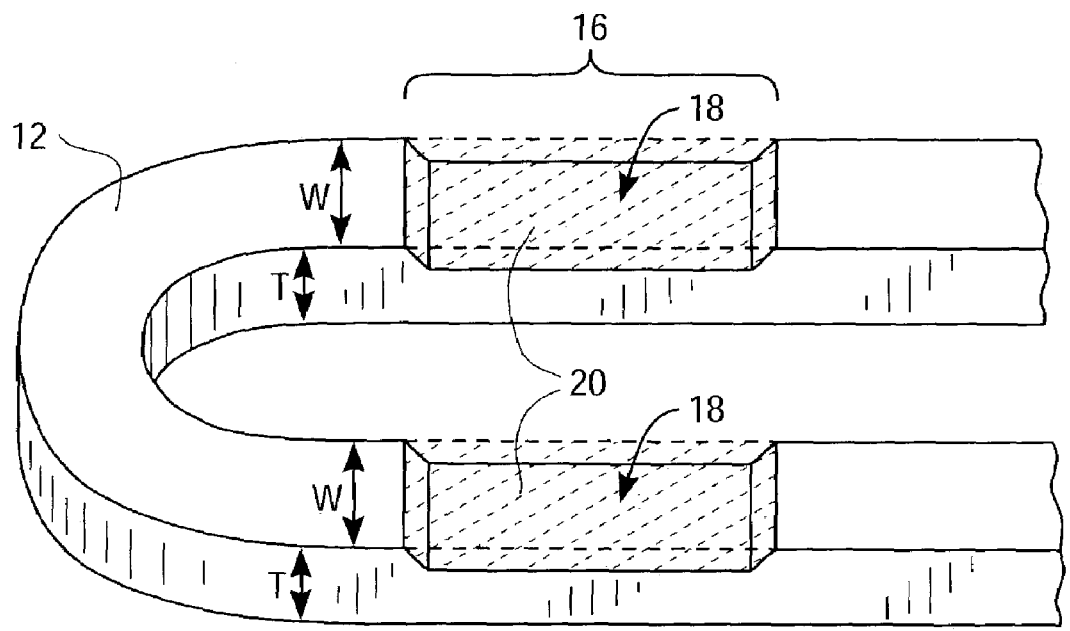
FIGS. 3, 4, 5, 6A, and 6B are perspective views of a stent strut according to other embodiments of the invention.

In accordance with another embodiment of the invention, as illustrated in FIG. 3, strut 12 can have a variable thickness T, but a constant width W. As best illustrated by FIG. 3, width W of strut 12 is the same, but thickness T is reduced along segment 16 of strut 12. The reduced thickness T provides recessed volume 18 containing coating 20 on the outer surface or tissue-contacting surface of strut 12. Although not illustrated, a recessed volume 18 can also be provided in the inner or lumen surface of strut 12.

Figure 4:
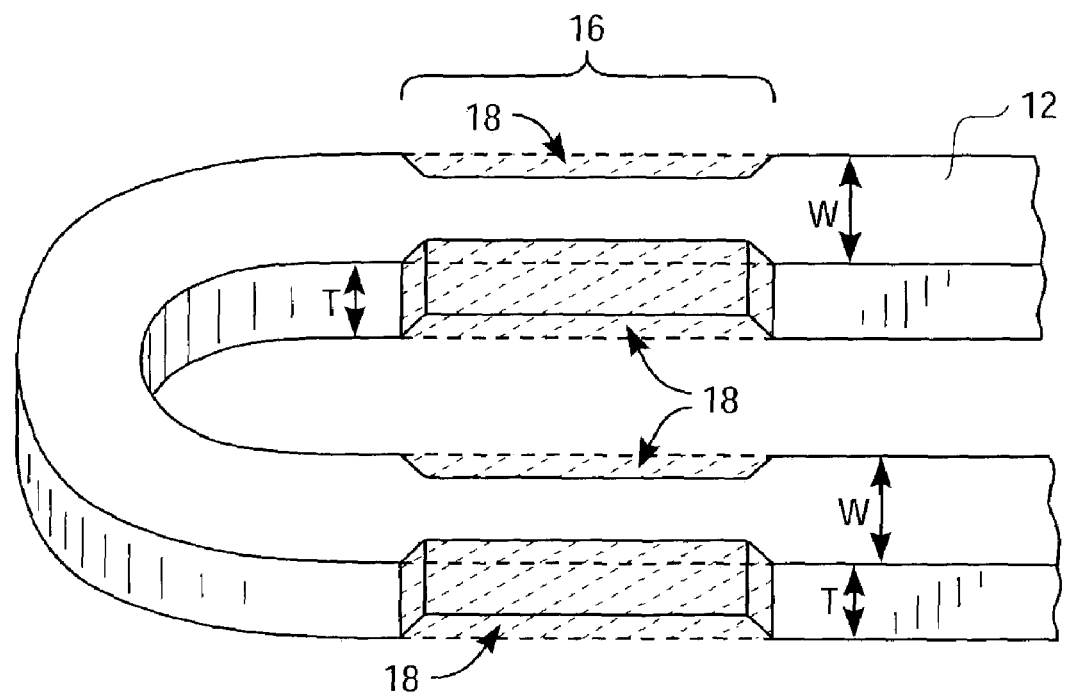

In accordance with another embodiment, as illustrated by FIG. 4, a variable width W for strut 12 can be provided, while maintaining the thickness T constant. As best illustrated by FIG. 4, thickness T of strut is the same, but width W is reduced along segment 16 of strut 12. FIG. 4 illustrates recessed volumes 18 on opposing sides of strut 12. However, as is the case with FIG. 3, recessed volume 18 can be about only one of the two sides of strut 12.

Transition zones leading into segment 16 can be gradual, with a slight slop, as illustrated by FIG. 2 or can be a relatively sharp drop-off, as illustrated by FIG. 3 or 4. The smallest transverse cross sectional area in segment 16 can be up to about 50% smaller than the transverse cross sectional area of the remaining portions of strut 12. One having ordinary skill in the art should be cautious of mechanical fatigue and failure that could be caused if the circumference of segment 16 is too small or if the transition zone is sloped too non-compliant. Exemplary dimensions and design of strut 12 depend, of course, on a variety of factors including the material from which strut 12 is made, the length of segment 16, and the application for which stent 10 will be used. Accordingly, there is a tradeoff between trying to maximize recess volume 18 for maximizing drug delivery capabilities and eliminating mechanical failure that can be caused by radial expansion and use of stent 10.

Figure 5:
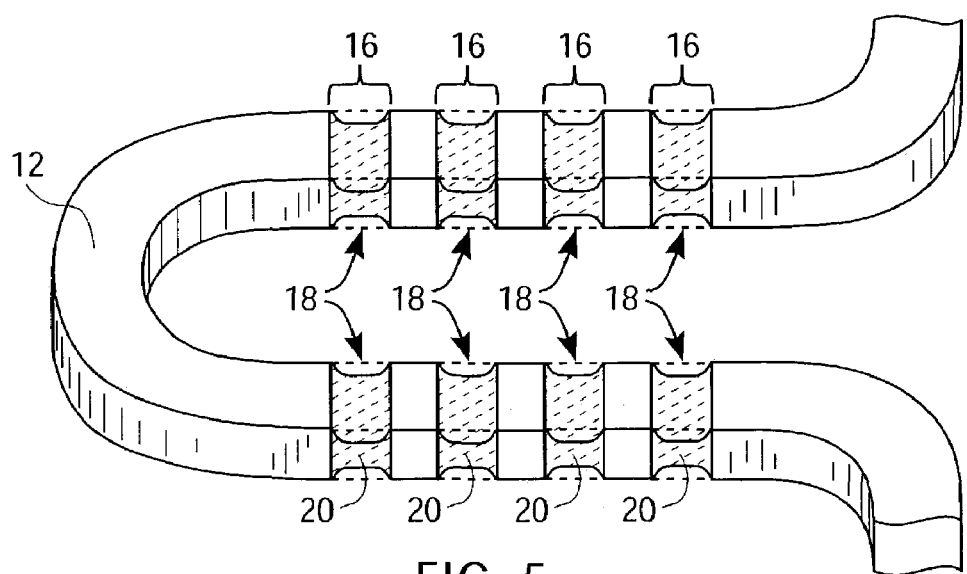

In accordance with yet another embodiment, as illustrated in FIG. 5, any number of suitable segments 16 having a reduced circumferential area can be included in strut 12. Having a multitude of segments 16 allows for the incorporation of more than one type of therapeutic substance in different areas of stent 10. Accordingly, a variety of cocktail combinations of drugs can be delivered via stent 10. The longitudinal span of each segment 16 depends on the number of segments 16 that are to be incorporated into strut 12 and the length of strut 12, among other factors.

Figure 6A:
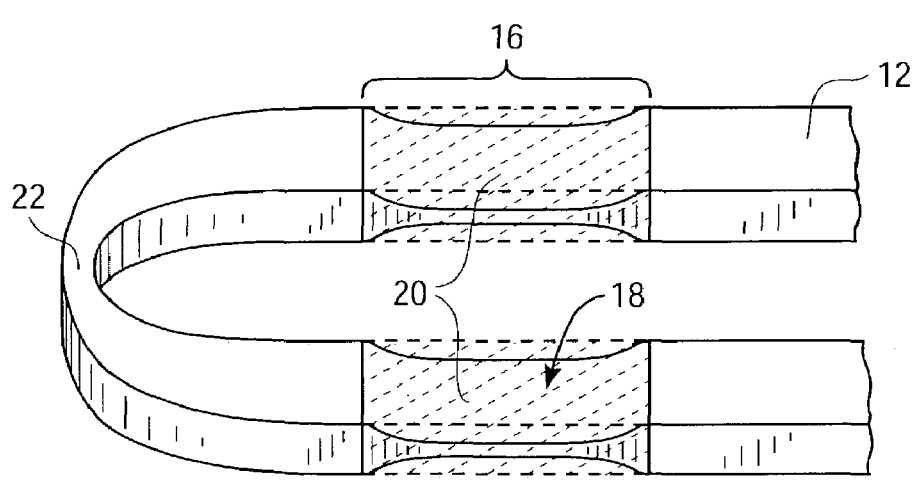
Figure 6B:
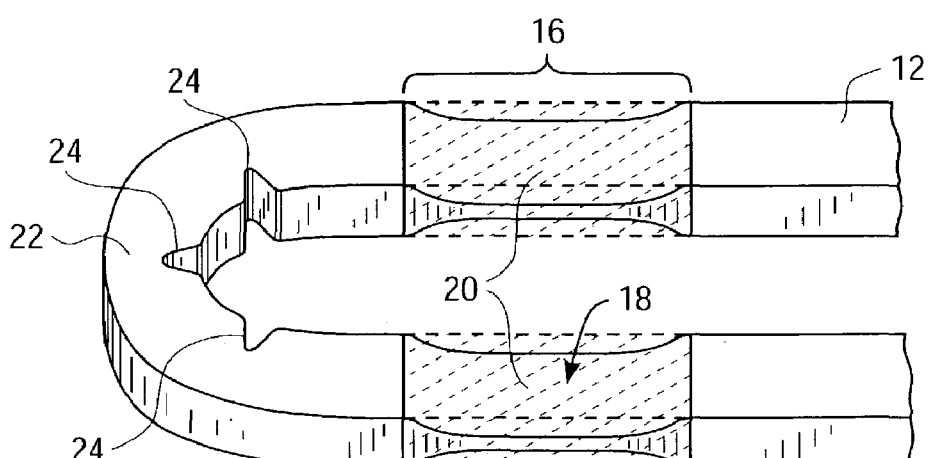

In accordance with yet another embodiment of the invention, FIG. 6A illustrates strut 12 having a thinned section, in either thickness or width, in the curved portion (as designated by reference number 22) of strut 12. Alternatively, as illustrated in FIG. 6B notches 24 can be provided in curved portion 22 of strut 12. The thinned section and/or pivot notches 24 in curved portion 22 of strut 12 can produce a weakened bending region for stent 10. The weakened bending region can maximize bending along curved region 22 or at pivot notches 24 and minimize stress along the linear portion of strut 12. This is advantageous in preserving the structural integrity of coating 20 so as to prevent or reduce fragmentation of coating during the radial expansion of stent 10.

Struts 12 can be made from a metallic material or an alloy such as, but not limited to, cobalt chromium alloy (EL-GILOY), stainless steel (316L), "MP35N," "MP20N," ELASTINITE (nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Struts 12 can also be made from bioabsorbable or biostable polymers.

The drug, therapeutic substance or active agent, terms which are used interchangeably, in the coating 20 can inhibit the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect for a diseased condition. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich, Inc., Milwaukee, Wis.; or COSMEGEN available from Merck & Co., Inc., Whitehorse Station, N.J.). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g., TAXOL® by Bristol-Myers Squibb Co., Stamford, Conn.), docetaxel (e.g., Taxotere®, from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack, N.J.), and mitomycin (e.g., Mutamycin® from Bristol-Myers Squibb Co.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co.), cilazapril or lisinopril (e.g., Prinivil® and Prinzide® from Merck & Co., Inc.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and its derivatives and analogs, and dexamethasone.

Coating 20 can be made from any suitable biocompatible polymer, examples of which include ethylene vinyl alcohol copolymer (commonly known by the generic name EVOH or by the trade name EVAL); poly(hydroxyvalerate); poly (L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly (ether-esters) (e.g., PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose. Coating 20 can also be silicon foam, neoprene, santoprene, or closed cell foam.

Stent 10 can be constructed, for example, from a tube of a desired strut material. The tube can be mounted onto a mandrel and angular grooves can be cut into the outer surface of the tube by a lathe or a Swiss screw, for example KJR-16 Swiss Screw Machine available from STAR CNC Automatic Lathe in Shizuoka, Japan. The shape of strut 12 can then be radially cut from the tube by a laser. The laser cutting can also produce the thinned curved section 22 or pivot notches 24 illustrated in FIGS. 6A and 6B. Struts 12 can be electropolished to reshape or round off sharp corners.

Stent 10 can then be mounted on a Teflon® or paralyne coated mandrel fixed to a two-dimensional actuator controlled by a computer numerical control (CNC) controller, for example a Model DR500 available from Aerotek, Inc., Pittsburgh, Pa. The two-dimensional actuator can translate and rotate stent 10 about the longitudinal axis of stent 10. A fluid applicator device, for example a Model 1500XL available from EFD, Inc., East Providence, R.I., with a needle tip, can be fixed adjacent to the mounted stent 10 and ejection of a coating substance can be controlled by the CNC controller. The needle tip can have an outer diameter of about 0.02 mm (0.0008 in.) to about 0.038 mm (0.0015 in.) and an inner diameter from about 0.005 mm (0.0002 in.) to about 0.02 mm (0.0009 in.). The CNC controller then causes ejection of coating 20 in a liquid state from the needle tip into recessed volume 18 and simultaneously moves stent 10 longitudinally to spread coating 20 evenly in recessed volume 18. Once recessed volume 18 of segment 16 is coated with a desired volume of coating 20, ejection of the coating substance ceases and stent 10 can be moved until the next uncoated recessed volume 18 is adjacent to the needle tip of the fluid applicator device. The process can repeat until all the recessed volumes 18 are coated. The needle tip should also be capable of being raised and lowered relative to stent 10 by the CNC controller particularly when coating small volumes necessitates direct contact between the needle tip and stent 10.

Alternatively, coating 20 can be deposited in recessed volumes 18 by crimping stent 10 onto a mandrel covered with a soft material (for examples, having a D hardness rating of about 20 to about 50, such as silicon foam, neoprene, santoprene, or a closed cell foam). In a relaxed state, the soft material can have, for example, a soft material thickness of at least the thickness of strut 12. The mandrel and stent 10 can then be dipped into the coating substance or the coating substance can be sprayed onto stent 10. The mandrel and stent 10 can then be pulled through an orifice with a clearance around strut 12 of less than about 0.003 mm (0.0001 in.), more narrowly less than about 0.001 mm (0.00005 in.). Stent 10 can also be pulled over a reamer to scrape off excess coating substance.

In accordance with another embodiment of the invention, masking techniques as is known to a person having ordinary skill in the art can be used to deposit coating 20 in recessed volumes 18 of segment 16.

While particular embodiments of the present invention have been shown and described, it will be obvious to those having ordinary skill in the art that changes and modifications can be made without departing from this invention. Therefore, the appended claims are to encompass within their scope all such changes and modifications as they fall within the true spirit and scope of the invention.

What is claimed is:

1. A stent, comprising:
 a strut having a first unitary segment, a second unitary segment and a third unitary segment along a length of the strut, the third unitary segment being located between the first and second unitary segments, wherein a circumference around the third unitary segment is less than a circumference around the first unitary segment and the circumference around the third unitary segment is less than a circumference around the second unitary segment, such that a recessed volume of the strut is provided at the third unitary segment, the recessed volume being all the way around the circumference of the third unitary segment; and a coating disposed all the way around the circumference of the third unitary segment including the recessed volume of the strut, wherein the first and second unitary segments of the strut are free of any coating.

2. The stent of claim 1, wherein the strut has a rectangular, triangular, oval or circular cross-sectional shape.

3. The stent of claim 1, wherein the coating is made from a polymeric material containing a therapeutic substance.

4. The stent of claim 1, wherein the strut includes a linear unitary segment extending into a curved or bent unitary segment, and wherein the first, second and third unitary segments define a part of the linear unitary segment of the strut.

5. The stent of claim 1, wherein an outer surface of the coating does not extend beyond an outer surface of the first and second unitary segments of the strut.

6. A stent, comprising:
a strut having a first segment, a second segment and a third segment located between the first and second segments, wherein the transverse cross-sectional area of the third segment is less than the transverse cross-sectional area of the first segment and the second segment such that a recessed volume of the strut is provided all the way around a circumference of the third segment, and wherein the strut includes a linear segment extending into a curved or bent segment, the first, second and third segments defining a part of the linear segment of the strut, wherein the curved or bent segment includes a notch carved out from the surface of the strut; and a coating disposed on the third segment of the strut, wherein the first and second segments of the strut are free of any coating.

7. The stent of claim 6, wherein the strut has a rectangular, triangular, oval or circular cross-sectional shape.

8. The stent of claim 6, wherein an outer surface of the coating does not extend beyond an outer surface of the first and second segments of the strut.

9. The stent of claim 6, wherein the coating includes a drug.

10. A stent, comprising:
a strut having a first unitary segment, a second unitary segment and a third unitary segment located between the first and second unitary segments, wherein the transverse cross-sectional area of the third unitary segment is less than the transverse cross-sectional area of the first unitary segment and the second unitary segment such that a recessed volume of the strut is provided all the way around a circumference of the third unitary segment, and wherein the strut includes a linear unitary segment extending into a curved or bent unitary segment, the first, second and third unitary segments defining a part of the linear unitary segment of the strut, wherein at least a unitary segment of the curved or bent unitary segment is smaller in thickness or width than the first or second unitary segment of the strut; and a coating disposed on the third unitary segment of the strut, wherein the first and second unitary segments of the strut are free of any coating.

11. The stent of claim 10, wherein the strut has a rectangular, triangular, oval or circular cross-sectional shape.

12. The stent of claim 10, wherein the coating includes a drug.

13. A radially expandable stent, comprising:
a unitary strut segment having four sides including two pairs of opposing sides, each of the opposing sides having an outer surface, wherein the outer surfaces of each pair of opposing sides face in different directions, wherein each of the outer surfaces of one pair of opposing sides has a unitary segment defined by a recessed volume completely filled with a coating substance.

14. The stent of claim 13, wherein a width of each of the outer surfaces of the other pair of opposing sides is smaller in the unitary segment including the recessed volume than a width of a remaining portion of the strut unitary segment.

15. The stent of claim 13, wherein a thickness of each of the outer surfaces of the other pair of opposing sides is smaller in the unitary segment including the recessed volume than a thickness of a remaining portion of the unitary strut segment.

16. The stent of claim 13, wherein the coating substance includes a polymeric material.

17. The stent of claim 13, wherein a remaining portion of the unitary strut segment is free from any coating.

18. The stent of claim 13, wherein the coating substance includes a therapeutic substance for the treatment of restenosis.

19. The stent of claim 13, wherein each of the outer surfaces of the other pair of opposing sides is free from the coating substance.

20. A method of manufacturing a stent, comprising:
depositing a coating on a first segment of a strut of the stent, the stent including a second segment and a third segment along the length of the strut, the first segment being positioned between the second segment and the third segment, wherein a circumference around the first segment is less than a circumference around the second segment and the circumference around the first segment is less than a circumference around the third segment, such that a recessed volume of the strut is provided at the first segment, the recessed volume being all the way around the circumference of the first segment, wherein the coating is disposed all the way around the circumference of the first segment including the recessed volume of the strut; and removing the coating off of the second and third segments so that the coating remains on the first segment.

21. The method of claim 20, wherein the strut has a rectangular, triangular, oval or circular cross-sectional shape.

22. The method of claim 20, wherein an outer surface of the coating does not extend beyond an outer surface of the second and third segments of the strut.

23. The method of claim 20, wherein the coating includes a drug.

24. A method of manufacturing a stent, comprising:
depositing a coating on a stent, the stent including a strut having a first segment, a second segment and a third segment along the length of the strut, the third segment located between the first and second segments, wherein the width of the third segment is less than the width of the first segment and of the second segment, and the thickness of the third segment is less than the thickness of the first segment and of the second segment, wherein the width and the thickness of the third segment are such that a recessed volume of the strut is provided at the third segment, the recessed volume being all the way around the circumference of the third segment; and removing the coating off of the first and second segments so that the coating remains on the third segment.

25. The method of claim 24, wherein an outer surface of the coating does not extend beyond an outer surface of the first and second segments of the strut.

26. The method of claim 24, wherein the coating includes a drug.

27. A stent, comprising:
a strut having a first unitary segment, a second unitary segment and a third unitary segment along the length of the strut, the third unitary segment being located between the first and second unitary segments, wherein the width of the third unitary segment is less than the width of the first unitary segment and of the second unitary segment, and the thickness of the third unitary segment is less than the thickness of the first unitary segment and of the second unitary segment, wherein the strut portion of the third unitary segment is free of recesses such that the recessed volume is not a recess; and
a coating disposed on the third segment of the strut, wherein the first and second unitary segments of the strut are free of any coating.

28. The stent of claim 27, wherein the coating is made from a polymeric material containing a therapeutic substance.

29. The stent of claim 27, wherein the strut includes a linear unitary segment extending into a curved or bent unitary segment, and wherein the first, second and third unitary segments define a part of the linear unitary segment of the strut.

30. The stent of claim 29, wherein the curved or bent unitary segment is smaller in thickness or width than the first or second unitary segment of the strut.

31. A stent comprising:
a strut having a first segment, a second segment and a third segment along the length of the strut, the third segment being located between the first and second segments, wherein the width of the third segment is less than the width of the first segment and of the second segment, and the thickness of the third segment is less than the thickness of the first segment and of the second segment, wherein the strut portion of the third segment is free of recesses such that the recessed volume is not a recess; and
a coating disposed on the third segment of the strut, wherein the first and second segments of the strut are free of any coating,
wherein an outer surface of the coating is fully filled and flush with an outer surface of the first or second segment of the strut.

32. A stent, comprising a strut having a first segment, a second segment and a third segment along the length of the strut, the third segment being located between the first and second segments, wherein the width of the third segment is less than the width of the first segment and of the second segment, and the thickness of the third segment is less than the thickness of the first segment and of the second segment, wherein the strut portion of the third segment is free of recesses; and
a coating disposed on the third segment of the strut, wherein the first and second segments of the strut are free of any coating,
wherein the strut includes a linear segment extending into a curved or bent segment, and wherein the first, second and third segments define a part of the linear segment of the strut,
wherein the curved or bent segment includes a notch carved out from the surface of the strut.

33. A stent, comprising a strut having a unitary segment defined by a recessed volume disposed all the way around a circumference of the strut, wherein a coating at least partially fills the recessed volume.

34. The stent of claim 33, wherein an outer surface of the coating does not extend beyond an outer surface of a nonrecessed portion of the strut.

35. The stent of claim 33, wherein the coating is made from a polymeric material containing a therapeutic substance.

36. The stent of claim 33, wherein the strut includes a linear unitary segment extending into a curved or bent unitary segment, and wherein the unitary segment defined by the recessed volume is a part of the linear unitary segment of the strut.

37. The stent of claim 36, wherein the curved or bent unitary segment includes a notch carved out from the surface of the strut.

38. The stent of claim 33, wherein the strut has a rectangular, triangular, oval or circular cross-sectional shape.

39. A method of manufacturing a stent, comprising depositing a coating substance on a stent, the stent including a unitary strut segment having four sides including two pairs of opposing sides, each of the opposing sides having an outer surface, wherein the outer surfaces of each pair of opposing sides face in different directions, wherein each of the outer surfaces of one pair of opposing sides has a unitary segment defined by a recessed volume, and wherein the coating substance completely fills at least one recessed volume.

40. The method of claim 39, wherein a width of each outer surface of the other pair of opposing sides is smaller in the unitary segment including the recessed volume than a width of a remaining portion of the unitary strut segment.

41. The method of claim 39, wherein a thickness of each outer surface of the other pair of opposing sides is smaller in the unitary segment including the recessed volume than a thickness of a remaining portion of the unitary strut segment.

42. The method of claim 39, wherein the coating substance includes a polymeric material.

43. The method of claim 39, wherein the coating substance includes a therapeutic substance for the treatment of restenosis.

44. A method of manufacturing a stent, comprising depositing a coating on a stent, the stent including a strut having a unitary segment defined by a recessed volume disposed all the way around a circumference of the strut.

45. The method of claim 44, wherein the coating includes a drug.

46. The method of claim 44, wherein the strut has a rectangular, triangular, oval or circular cross-sectional shape.

47. The method of claim 44, wherein an outer surface of the coating does not extend beyond an outer surface of the strut.

48. The method of claim 44, wherein the strut includes a linear segment extending into a curved or bent segment, and wherein the segment defined by the recessed volume is a part of the linear segment of the strut.

49. The method of claim 48, wherein the curved or bent segment includes a notch carved out from the surface of the strut.

50. A radially expandable stent, comprising a unitary strut segment having four sides including two pairs of opposing sides, each of the opposing sides having an outer surface, wherein the outer surfaces of each pair of opposing sides face in different directions, wherein an outer dimension of each outer surface of one pair of opposing sides is less than an outer dimension of a remaining portion of the unitary strut segment so that each outer surface of the other pair of opposing sides has a unitary segment defined by a recessed volume, and wherein the recessed volume is at least partially filled with a coating substance.

51. The stent of claim 50, wherein the coating substance includes a drug.

52. The stent of claim 50, wherein the strut includes a linear segment extending into a curved or bent segment, and wherein the segment defined by the recessed volume is a part of the linear segment of the strut.

53. The stent of claim 52, wherein the curved or bent segment includes a notch carved out from the surface of the strut.

54. A stent comprising:
a strut having a first segment, a second segment and a third segment located between the first and second segments, wherein the transverse cross-sectional area of the third segment is less than the transverse cross-sectional area of the first segment and the second segment such that a recessed volume of the strut is provided all the way around a circumference of the third segment, and wherein the strut includes a linear segment extending into a curved or bent segment, the first, second and third segments defining a part of the linear segment of the strut, wherein at least a segment of the curved or bent segment is smaller in thickness or width than the first or second segment of the strut; and
a coating disposed on the third segment of the strut, wherein the first and second segments of the strut are free of any coating,
wherein an outer surface of the coating does not extend beyond an outer surface of the first and second segments of the strut.

55. A method of manufacturing a stent, comprising:
depositing a coating on a stent, the stent including a strut having a first segment, a second segment and a third segment located between the first and second segments, wherein the transverse cross-sectional area of the third segment is less than the transverse cross-sectional area of the first segment and the second segment such that a recessed volume of the strut is provided all the way around a circumference of the third segment, and wherein the strut includes a linear segment extending into a curved or bent segment, the first, second and third segments defining a part of the linear segment of the strut, wherein at least a segment of the curved or bent segment is smaller in thickness or width than the first or second segment of the strut; and
removing the coating off of the first and second segments so that the coating remains on the third segment.

56. The method of claim 55, wherein the coating includes a drug.

57. The method of claim 55, wherein the strut has a rectangular, triangular, oval or circular cross-sectional shape.

58. The method of claim 55, wherein an outer surface of the coating does not extend beyond an outer surface of the strut.

59. A method of manufacturing a stent, comprising:
depositing a coating on a stent, the stent including a strut segment having four sides including two pairs of opposing sides, each of the opposing sides having an outer surface, wherein the outer surfaces of each pair of opposing sides face in different directions, wherein an outer dimension of each outer surface of one pair of opposing sides is less than an outer dimension of a remaining portion of the strut segment so that each outer surface of the other pair of opposing sides has a segment defined by a recessed volume, and wherein the coating is carried by at least one recessed volume; and
removing the coating from each outer surface of the pair of opposing sides without the recessed volume so that the coating remains in the at least one recessed volume.

60. The method of claim 59, wherein the coating includes a drug.

61. The method of claim 59, wherein the strut has a rectangular, triangular, oval or circular cross-sectional shape.

62. The method of claim 59, wherein an outer surface of the coating does not extend beyond the outer surfaces of the strut.

* * * * *